US011490901B2

(12) United States Patent
Atkin et al.

(10) Patent No.: US 11,490,901 B2
(45) Date of Patent: Nov. 8, 2022

(54) FEMORAL NECK RESECTION GUIDE

(71) Applicant: DEPUY IRELAND UNLIMITED COMPANY, Ringaskiddy (IE)

(72) Inventors: Jamie Atkin, Leeds (GB); David Beverland, Leeds (GB); Sarah Bushell, Leeds (GB); Oliver Coultrup, Leeds (GB); Graeme Dutton, Leeds (GB); Jason Naylor, Leeds (GB); Stephen Robinson, Leeds (GB)

(73) Assignee: DEPUY IRELAND UNLIMITED COMPANY

( * ) Notice: Subject to any disclaimer, the term of this patent is extended or adjusted under 35 U.S.C. 154(b) by 0 days.

(21) Appl. No.: 17/251,251

(22) PCT Filed: Jun. 24, 2019

(86) PCT No.: PCT/EP2019/066612
§ 371 (c)(1),
(2) Date: Dec. 11, 2020

(87) PCT Pub. No.: WO2020/002198
PCT Pub. Date: Jan. 2, 2020

(65) Prior Publication Data
US 2021/0259706 A1 Aug. 26, 2021

(30) Foreign Application Priority Data

Jun. 26, 2018 (GB) .................... 1810475
Aug. 17, 2018 (GB) .................... 1813421
Apr. 17, 2019 (GB) .................... 1905474

(51) Int. Cl.
*A61B 17/15* (2006.01)
(52) U.S. Cl.
CPC ............ *A61B 17/155* (2013.01); *A61B 17/15* (2013.01)

(58) Field of Classification Search
CPC ..... A61B 17/15; A61B 17/154; A61B 17/155; A61B 17/74; A61B 17/90; A61F 2/4657; A61F 2002/4687
See application file for complete search history.

(56) References Cited

U.S. PATENT DOCUMENTS 4,621,630 A 11/1986 Kenna
4,959,066 A 9/1990 Dunn et al.
(Continued)

FOREIGN PATENT DOCUMENTS

AU 2006200152 A1 8/2006
EP 1797834 A1 6/2007
(Continued)

OTHER PUBLICATIONS

WO International Search Report application No. PCT/EP2019/060976, dated Jul. 8, 2019.
(Continued)

*Primary Examiner* — Larry E Waggle, Jr.

(57) ABSTRACT

The invention provides a surgical device for performing a controlled resection of the neck of a femur during a hip replacement procedure. The surgical device comprises a body portion having: a frame comprising an aperture dimension for receipt of a femoral head of the femur to position the body portion with respect to a centre of the femoral head; a resection guide for indicating a position of a resection plane on the femoral neck, and an arm extending between the frame and the resection guide. The body portion includes a linear alignment surface for alignment with a femoral shaft axis of the femur while the frame is mounted on the anterior or posterior aspect of the femoral head.

24 Claims, 16 Drawing Sheets

(56) References Cited

U.S. PATENT DOCUMENTS

| | | | |
|---|---|---|---|
| 5,464,406 A | 11/1995 | Ritter et al. | |
| 5,578,037 A | 11/1996 | Sanders | |
| 5,607,431 A | 3/1997 | Dudasik et al. | |
| 6,258,097 B1 | 7/2001 | Cook et al. | |
| 6,421,630 B1 | 7/2002 | Yamada et al. | |
| 6,503,255 B1 | 1/2003 | Albrektsson | |
| 7,582,091 B2 | 9/2009 | Duncan et al. | |
| 7,601,155 B2 * | 10/2009 | Petersen | A61B 17/175 |
| | | | 606/85 |
| 7,833,275 B2 | 11/2010 | Mears et al. | |
| 8,246,621 B2 | 8/2012 | Poncet | |
| 8,821,499 B2 * | 9/2014 | Iannotti | A61F 2/4603 |
| | | | 606/87 |
| 8,939,982 B2 * | 1/2015 | Chellaoui | A61B 17/175 |
| | | | 606/86 R |
| 2003/0009170 A1 | 1/2003 | Tornier | |
| 2004/0122439 A1 | 6/2004 | Dwyer | |
| 2004/0236341 A1 | 11/2004 | Petersen | |
| 2014/0276866 A1 | 9/2014 | Endsley | |

FOREIGN PATENT DOCUMENTS

| | | |
|---|---|---|
| TW | 201540251 A | 11/2015 |
| WO | 2002/026145 A1 | 4/2002 |
| WO | 2003/009170 A1 | 1/2003 |
| WO | WO2005/110250 A1 | 11/2005 |
| WO | 2020/001830 A1 | 1/2020 |
| WO | 2020/001832 A1 | 1/2020 |
| WO | 2020/002190 A1 | 1/2020 |

OTHER PUBLICATIONS

WO International Search Report Application No. PCT/EP2019/066612, dated Oct. 1, 2019.
WO International Search Report Application No. PCT/EP 2019/060894, dated Aug. 9, 2019.
WO International Search Report Application No. PCT/EP2019/066596, dated Oct. 7, 2019.

* cited by examiner

FEMORAL NECK RESECTION GUIDE

CROSS-REFERENCE TO RELATED APPLICATIONS

This application is a National Stage Application filed Under 35 U.S.C. § 371 of International Application No. PCT/EP2019/066612 filed Jun. 24, 2019, which claims priority to GB1810475.2 filed Jun. 26 2018 and GB1813421.3 filed Aug. 17, 2018 and GB1905474.1 filed Apr. 17, 2019, all of which are hereby incorporated by reference in their entireties.

FIELD OF THE INVENTION

This invention relates to a surgical device and method for performing a controlled resection of the neck of a femur during a hip replacement procedure.

BACKGROUND OF THE INVENTION

Hip replacement is a surgical procedure in which the hip joint is replaced by a prosthetic implant. In total hip replacement surgery, a patient's natural hip is replaced by an acetabular cup component that replaces the acetabular socket and a femoral component that replaces the femoral head.

During such a surgical procedure, a diseased portion of the femur is excised, usually by removing the femoral head prior to milling of the calcar face. A prosthetic femoral component and a prosthetic femoral head replace the natural structures that are surgically removed. The positioning of the femoral component of the prosthesis is important to ensure proper fit and smooth rotation of the femoral head within its socket (i.e., the acetabular shell).

If the surgeon removes too much of the femur at the resection stage, joint tension will have to be manipulated during later stages of the surgical procedure. This can be achieved by increasing head offset or by switching to a high offset neck trial. Both of these approaches would deviate from the optimal surgical plan, potentially increasing the risk of poor post-surgery biomechanics and patient outcome.

Not removing enough bone can make it harder to mill the calcar face effectively, increase bone fragments in the wound space and reduce the performance and life of the calcar mill instrument. Additionally, this leads to inefficiency in the surgical process, associated costs and a reduction in the free space within the wound cavity.

When performing joint reconstruction, such as hip replacement surgery, it is important that the pre-surgical geometry of the bone structure is replicated in the post-surgical structure. It is important to maintain the natural joint biomechanics, ensuring proper joint and soft tissue balancing. If this is not achieved, the result can be higher joint forces, and overall joint instability.

It is therefore necessary to ensure that orthopedic implant structures are properly placed within a patient. In the case of hip joint prostheses, it is important that the native anatomic centre of rotation of the femoral head within the acetabular shell be located and maintained during the implantation of the replacement structure. Misplacement of the centre of rotation during implantation of the femoral component of the hip joint prosthesis can affect the patient's leg length can lead to a very unsatisfactory result for the patient.

It is important in primary total hip arthroplasty to determine the natural offset and neck length of the femoral head by measurement. Offset can be measured from a point on the greater trochanter to the centre of the femoral head. Neck length can be measured from a point of the lesser trochanter to the centre of the femoral head.

U.S. Pat. No. 6,258,097 discloses an orthopaedic instrument for comparing post-surgical joint geometry to pre-surgical joint geometry. The instrument includes a head chuck that can be secured to the ball of a ball joint, and an arm having reference indicia thereon. Markings indicative of the pre-surgical joint geometry are made on the bone with reference to the centre of the ball joint. After replacement with a prosthetic ball, the post-operative geometry is verified by securing the head chuck to the prosthetic ball, and comparing the location of the bone markings against the reference indicia on the arm. As needed, adjustments are made in the prosthetic components.

There remains a need for surgical instruments that will assist surgeons to resect the femoral neck at the appropriate resection plane in order to reproduce within the artificial joint the hip's anatomic centre of rotation. Furthermore, the current resection guides do not take into account the variety of head offsets that can be templated and so leaves the surgical procedure open to an increase risk of error.

SUMMARY OF THE INVENTION

Aspects of the invention are set out in the accompanying independent and dependent claims. Combinations of features from the dependent claims may be combined with features of the independent claims as appropriate and not merely as explicitly set out in the claims.

According to a first aspect of the invention there is provided a surgical device for performing a controlled resection of the neck of a femur during a hip replacement procedure, the surgical device comprising:
 a body portion having:
 a frame comprising an aperture, wherein the aperture is dimensioned for receiving a femoral head of the femur to position the body portion with respect to a centre of the femoral head;
 a resection guide for indicating a position of a resection plane on the femoral neck, and
 an arm extending between the frame and the resection guide, wherein the body portion includes a linear alignment portion for alignment with the femoral shaft axis of the femur while the frame is mounted on the femoral head.

The Frame

An imaginary line dissects the frame through its centrepoint into a medial portion and a lateral portion. When the frame is mounted on the femoral head via receipt of the femoral head in the aperture, the medial portion is located toward the anatomical median plane.

In some constructions of the surgical device, the linear alignment surface is provided within the medial portion of the frame. For example, the frame may have a generally circular outer perimeter edge, and a linear alignment surface is provided within at least a part of the outer perimeter edge of the medial portion of the device.

In some other constructions of the surgical device, the linear alignment surface is provided within the lateral portion of the frame. For example, the frame may have a generally circular outer perimeter edge, and a linear alignment surface is provided within at least a part of the outer perimeter edge of the lateral portion of the device. Provision of the linear alignment surface on the lateral portion of the device is advantageous for correctly aligning the device on either the right femoral head or the left femoral head when a surgeon uses a posterior approach during hip arthroplasty.

The frame may include markings which inform the surgeon of the orientation that the surgical device should be used when mounted on the right femoral head or the left femoral head, and dependent on whether the surgeon is using an anterior approach or the posterior approach. Markings may take the form of, for example: "left anterior", "L-ANT", "right posterior" or "R-Post". When a surgeon is using the surgical device in a posterior approach, (s)he will mount the frame on the left femoral head with the appropriate orientation marking (e.g., "left posterior") visible. When a surgeon is using the surgical device on a right femoral head in a posterior approach, (s)he will mount the frame on the right femoral head with appropriate marking (e.g., "right posterior") visible.

The frame may include at least one pin hole configured for removable receipt of a bone pin for removably mounting the frame on the femoral head.

The linear alignment surface provided within the medial portion or the lateral portion of the frame may be parallel with the imaginary line that divides the frame into the medial half and the lateral half.

The frame may be provided with more than one linear alignment surface. For example, a first linear alignment surface may be provided on the medial portion of the frame, and a second linear alignment surface may be provided on the lateral portion of the frame.

As discussed above, the first imaginary line extends through the centrepoint of the frame and divides the frame into a medial portion and a lateral portion. A second imaginary line, being orthogonal to the first imaginary line, extends through the centrepoint of the frame and divides the frame into a superior portion and an inferior portion. The first imaginary line and the second imaginary line subdivide the frame into quadrants: a lateral superior quadrant, a lateral inferior quadrant, a medial superior quadrant and a lateral inferior quadrant.

In some constructions, the outer perimeter edge of at least one quadrant of the frame is defined by two perpendicular linear alignment surfaces. Accordingly, the quadrant includes a corner. The provision of a corner improves the alignment and holding of the surgical device. At least one of the lateral superior quadrant, a lateral inferior quadrant, a medial superior quadrant and a lateral inferior quadrant includes a corner. In some constructions, each of the lateral superior quadrant and the medial inferior quadrant include a corner.

In some constructions, the one or more linear alignment surfaces is/are only provided on the frame.

Femoral offset is the distance between the centre of rotation of the femoral head to a line bisecting the long axis of the femur. Normal femoral offset varies between 30 mm and 60 mm.

A decrease in femoral offset moves the femur closer to the pelvis medially. This can lead to impingement of the greater trochanter. The medial movement may also result in soft tissue relaxation. Both of these factors can lead to instability of the implant and possible dislocation. When the offset decreases, greater force is required by the abductor muscles to balance the pelvis and resultant forces across the hip joint also increases resulting in greater wear and tear.

An increase in femoral offset moves the femur laterally resulting in a decreased chance of impingement, a better tension and a better stability. An increase in femoral offset decreases the force required by the abductor muscles to balance the pelvis, which will improve gait and may result in less wear and loosening over time.

A change in femoral offset does not affect the leg length.

In some constructions, the frame includes indicia representative of femoral offset.

The indicia may be arranged on the frame in the form of a graduated scale. The scale may comprise a plurality of linear features, whereby each linear feature is representative of a specific femoral offset.

Each linear feature may be a line etched into or laser marked onto the surface of the frame. Alternatively, each linear feature may be a slot provided about the inner perimeter of the frame.

The graduated scale may be referred to as primary indicia.

The primary indicia may be coded in a manner that visually informs the surgeon of the actual femoral offset as measured in millimetres (mm) that it is representative of. For example, the scale may be colour coded. A red line or edging to a slot may be representative of a first femoral offset (e.g., +15 mm), whilst a green line or edging to a slot may be representative of a second femoral offset (e.g., −2 mm).

In order to achieve a selected femoral offset the surgeon moves the frame over the femoral head to align one of the plurality of primary indicia with the centre of the femoral head. This alignment will have the effect of moving the resection plane to a position that will achieve the selected femoral offset.

A surgeon may select the femoral offset of the final hip implant to match the patient's anatomical femoral offset.

The aperture of the frame may be substantially circular or substantially oval. An oval aperture aids movement of the frame over the femoral head when aligning a selected linear feature of the graduated scale with the femoral head centre.

Secondary indicia, for example in a numerical format representative of the actual femoral offset as measured in millimetres (mm) may be associated with (e.g., provided adjacent to) the primary indicia. For example, for an exemplary implant system the secondary indicia may be selected from the group consisting of −2 mm, +1.5 mm, +5 mm, +8.5 mm, +12 mm and +15.5 mm.

The indicia may be provided on both faces of the frame. This allows femoral offset to be accounted for regardless of the surgical approach (e.g., posterior or anterior) on either the right hip or the left hip. This is advantageous as it reduces the inventory of guides required.

The Arm

The arm forms a bridge between the frame and the resection guide. The arm extends from an inferior edge of the frame.

The length of arm may vary between different constructions of the surgical device, thereby providing surgical devices for indicating different resection planes.

The arm has a medial edge and a lateral edge.

In some constructions, the arm is not provided with a linear alignment surface. Instead, the medial and/or lateral edge of the arm, may have a curved surface.

In some other constructions, the linear alignment surface is provided on either the medial edge or the lateral edge of the arm. Optionally, the arm may have more than one linear alignment surface. For example, a first linear alignment surface is provided on the medial edge of the arm, and a second linear alignment surface is provided on the lateral edge of the arm.

In some constructions, the one or more linear alignment surfaces is/are only provided on the arm.

It is however envisaged that the frame and the arm may each include one or more linear alignment surfaces.

For example, a first linear alignment surface may be provided on the medial portion of the frame and a second linear alignment surface may be provided on the medial edge of the arm. These medially located linear alignment surfaces may be collinear.

It is also further envisaged that in other constructions of the surgical device, a first linear alignment surface may be provided on the lateral portion of the frame and a second linear alignment surface may be provided on the lateral edge of the arm. These laterally located linear alignment surfaces may be collinear The linear alignment surface, whatever its location is on the surgical device, should be of a sufficient length such that it is readily obvious to the surgeon as being a linear alignment surface which is to be aligned with the femoral shaft axis.

Resection Guide

The resection guide may include a first longitudinal outer edge that defines a first resection guide surface for indicating a position of a first resection plane (i.e., a calcar cut angle) on the femoral neck.

The resection guide may include a second longitudinal outer edge that defines a second resection guide surface for indicating a position of a second resection plane (i.e., a calcar cut angle) on the femoral neck.

The first resection guide surface may be located superior of the second resection guide surface. The first resection guide surface may represent a resection plane that corresponds to a standard offset neck resection plane, whilst the second resection guide surface may represent a resection plane that corresponds to a high offset neck resection plane.

In some constructions of the resection guide, the first and second resection guide surfaces are parallel. This results in the femoral neck shaft angle formed between the prosthetic neck shaft axis and the femoral shaft axis being the same, whether the femoral neck has been resected along a first resection plane (corresponding to the first resection surface) or along a second resection plane (corresponding to the second resection surfaces). For example, a femoral neck shaft angle of about 135° is formed by resection of the femoral neck along the first or second resection plane.

In some constructions of the resection guide, the first and second resection guide surfaces are non-parallel, for example, they taper to a point. This design of resection guide results in the femoral neck shaft angle formed between the prosthetic neck shaft axis and the femoral shaft axis that differs dependent on which resection surface has been used. For example, the femoral neck shaft angle formed between the prosthetic neck and the femoral shaft axis may be $\theta^X$ (e.g., about 125°) if the femoral neck has been resected along a first resection plane (corresponding to the first resection surface). The second femoral neck shaft angle may $\theta^Y$ (e.g., about 135°) if the femoral neck has been resected along a second resection plane (corresponding to the second resection surface).

The resection guide of the surgical device may also include a guide slot for indicating a position of a resection plane (e.g., standard offset neck resection plane or high offset neck resection plane) on the femoral neck. The resection guide may include more than one guide slots. For example, a first guide slot for indicating a standard offset neck resection plane, and a second guide slot for indicating a high offset neck resection plane. The guide slot may be used for marking the neck resection plane on the femoral neck and/or for receiving a blade of a cutting device for cutting along the resection plane.

Markings on the resection guide (e.g., STD, HI) may be provided to indicate to the surgeon which resection guide surface or guide slot should be used to mark and/or cut along in order to produce a standard neck offset or a high neck offset resection cut.

In some constructions, the surgical device includes a single arm forming a bridge to a single resection guide.

In some other constructions, the surgical device comprises a plurality of arms and a plurality of resection guides, each arm forming a bridge between the frame and a respective resection guide. This design allows a single surgical device to be used for illustrating to a surgeon the position of a resection plane that will provide differing femoral head offsets.

The device may include at least a first aim forming a bridge with a first resection guide, a second arm forming a bridge with a second resection guide, and a third arm forming a bridge with a third resection guide.

Rotation of the device to align a linear alignment surface on the first arm can be used to indicate a standard or high offset neck resection plane corresponding to a first femoral head offset.

Rotation of the device to align a linear alignment surface on the second arm can be used to indicate a standard or high offset neck resection plane corresponding to a second femoral head offset.

Rotation of the device to align a linear alignment surface on the third arm can be used to indicate a standard or high offset neck resection plane corresponding to a third femoral head offset.

Spacer

It has been found that if the resection guide of the device is not in a substantially vertical position relative to the femoral head, (lying parallel to the femoral coronal plane) the indicated position of the resection plane may be inaccurate. Advantageously therefore, a spacer may be mounted on the resection guide to space the underside of the resection guide away from the femoral neck. This spacer can also assist in defining the plane of the neck cut.

The resection guide has a first surface and a second opposing surface. The spacer is provided on at least one of the first surface and the second opposing surface for spacing the resection guide away from the femoral neck.

The spacer may be removably mountable on the resection guide. For example a "clip-on" spacer. Alternatively, the spacer may permanently attached to the resection guide. In some instances, the spacer may be moulded as part of the resection guide.

The spacer may take the form of a rectangular block.

Different lengths of spacer may be used. In some constructions, the spacer may have the same length as the resection guide. However, this may obstruct the surgical process and may also make the surgical device less stable. A suitable length of spacer has been found to be about 10 mm. This is as a non-limiting example and should not be taken as any limitation of the length of the spacer.

Different depths of spacer may be used. In some constructions, the spacer may have the same depth as the resection guide. A suitable depth of spacer has been found to be about 6 mm. This is as a non-limiting example and should not be taken as any limitation of the depth of the spacer.

The surgical device may be manufactured as a single unitary component. For example, the surgical device may be 3D printed.

According to a second aspect of the invention there is provided a surgical kit for use in performing a controlled resection of the neck of a femur during a hip replacement procedure, the surgical kit comprising a
  a surgical device comprising:
    a body portion having
      a frame comprising an aperture, wherein the aperture is dimensioned for receiving a femoral head of the femur to position the body portion with respect to a centre of the femoral head;
      a resection guide for indicating a position of a resection plane on the femoral neck, and
      an arm extending between the frame and the wherein the body portion includes a linear alignment surface for alignment with a femoral shaft axis of the femur whilst the frame is mounted on the femoral head, and
    a spacer that is removably mountable on the resection guide.

According to a third aspect of the invention there is provided a surgical kit for use in performing a controlled resection of the neck of a femur during a hip replacement procedure, the surgical kit comprising a
  a first surgical device comprising:
    a body portion having:
      a frame comprising an aperture, wherein the aperture is dimensioned for receiving a femoral head of the femur to position the body portion with respect to a centre of the femoral head;
      a resection guide for indicating a position of a resection plane on the femoral neck, and
      an arm extending between the frame and the resection guide,
    wherein the body portion includes a linear alignment surface for alignment with a femoral shaft axis of the femur whilst the frame is mounted on the femoral head, and
  a second surgical device comprising:
    a body portion having:
      a frame comprising an aperture, wherein the aperture is dimensioned for receiving a femoral head of the femur to position the body portion with respect to a centre of the femoral head;
      a resection guide for indicating a position of a resection plane on the femoral neck, and
      an arm extending between the frame and the resection guide,
    wherein the body portion includes a linear alignment surface for alignment with a femoral shaft axis of the femur whilst the frame is mounted on the femoral head, and wherein the arm of the first device has a first length as measured between the frame and resection guide, and the arm of the second device has a second length as measured between the frame and resection guide, and wherein the first length and the second length are different.

According to a fourth aspect of the invention there is provided a method for performing a controlled resection of the neck of a femur during a hip replacement procedure using a surgical device comprising:
  a body portion having:
    a frame comprising an aperture, wherein the aperture is dimensioned for receiving a femoral head of the femur to position the body portion with respect to a centre of the femoral head;
    a resection guide for indicating a position of a resection plane on the femoral neck, and
    an arm extending between the frame and the resection guide,
  wherein the body portion includes a linear alignment surface for alignment with a femoral shaft axis of the femur whilst the frame is mounted on the femoral head, the method comprising:
    mounting the frame on the femoral head;
    aligning the linear alignment surface on the body portion along the femoral shaft axis of the femur, and using the resection guide to either:
    mark the position of the resection plane on the neck of the femur; or
    guide a blade of a cutting device to resect the neck of the femur.

When performing a controlled resection of the neck of a femur during a hip replacement procedure the frame may be removably mounted on a posterior aspect of the femoral head, or on an anterior aspect of the femoral head.

The method may further include the step of measuring the femoral head offset of the native femoral head and of the trial prosthetic femoral head. This involves measuring the horizontal distance from the femoral head centre to a marked point on the greater trochanter. A comparison of the measurements will provide an indication as to whether the anatomical femoral head centre has been restored in the trial and thus the definitive prosthetic reconstruction of the hip.

The method step of measuring the native femoral head offset may comprise the steps of:
  (a) placing the frame on the native femoral head;
  (b) marking a cross on the native femoral head to indicate the native femoral head centre, wherein the vertical line of said cross is substantially parallel to the femoral shaft axis;
  (c) placing a rule parallel to the horizontal line of the cross on the native femoral head and marking a further (aligned) horizontal line on the adjacent greater trochanter;
  (d) marking a vertical line at an arbitrary point along the horizontal line marked in step (c) above; and
  (e) measuring the dimension $D_1$ between the femoral head centre identified in step (b) above and the vertical mark marked in step (d) above;

The marking in steps (b), (c) and (d) above may be undertaken using a pen. The method step of measuring the trial femoral head offset may comprise the steps of:
  (f) placing a trial femoral neck and head assembly onto the proximal end of a broach located in situ within the femoral shaft, preferably the head component of the assembly comprises a posterior aspect with a planar portion on which a cross defined by a substantially vertical line and a substantially horizontal line is marked, the intersection of the vertical line and the horizontal line indicating the femoral head centre;
  (g) checking that the horizontal line on the trial femoral head is aligned with the horizontal line marked on the greater trochanter in step (c) above, and
  (h) measuring the distance $D_2$ from the femoral head centre of the trial femoral head to the vertical line marked on the greater trochanter in step (d) above.

The alignment of the two horizontal lines in step (g) ensures that the vertical height of the trial femoral head is consistent with the anatomic vertical height of the native femoral head.

Ensuring that the value of $D_1$ measured in step (e) above is substantially the same as the value of $D_2$ measured in step (h) above ensures that the anatomic femoral head offset is restored by the trial prosthetic head.

BRIEF DESCRIPTION OF THE DRAWINGS

Constructions of the present invention will be described hereinafter, by way of example only, with reference to the accompanying drawings in which like reference signs relate to like elements and in which.

DETAILED DESCRIPTION

Figure 1:
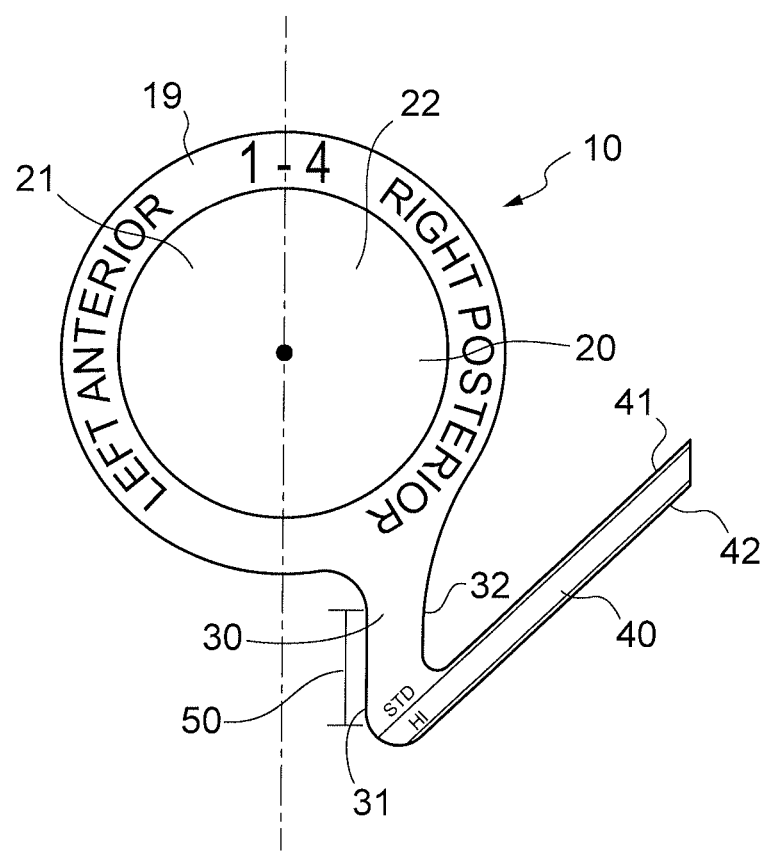
FIG. 1: Illustrates a schematic of a first exemplary construction of the surgical device according to the invention.

FIG. 1 illustrates a first construction of the surgical device 10 according to the invention. The device includes a frame 19 having an aperture 20 for mounting the frame of the device on a femoral head. The device also includes an arm 30 and a resection guide 40. The arm extends from an inferior edge of the frame to the resection guide.

The surgical device may be used with different hip systems.

First Exemplary Hip System

In the first exemplary hip system, the femoral stem components are grouped into three, based upon stem size.
Group 1: Stem sizes 1-4.
Group 2: Stem sizes 5-8.
Group 3: Stem sizes 9-12.

The neck length increases incrementally (e.g., by about 0.9 mm) for each stem size within each Group for a standard offset neck. The neck length increases incrementally (e.g., by about 1.2 mm) for each stem size within each Group for a high offset neck.

For example, the size 1 standard offset neck femoral stem component in Group 1 has a neck length of about 28.6 mm, whilst the size 3 standard offset neck femoral stem component in Group 1 has a neck length of about 30.2 mm.

For example, the size 9 standard offset neck femoral stem component in Group 3 has a neck length of about 35.8 mm, whilst the size 12 standard offset neck femoral stem component in Group 3 has a neck length of about 38.2 mm.

As such, the system is referred to as "progressive" neck system.

Three constructions of the surgical device according to the invention may be provided for use with this first exemplary hip system.

A first construction of the surgical device is configured for use in conjunction with sizes 1-4 of the femoral stem component. The resection guide surfaces of the surgical device indicate a Standard Offset 135° resection plane and a High Offset 135° resection plane.

A second construction of the surgical device is configured for use in conjunction with sizes 5-8 of the femoral neck component. The resection guide surfaces of the surgical device indicate a Standard Offset 135° resection plane and a High Offset 135° resection plane.

A third construction of the surgical device is configured for use in conjunction with sizes 9-12 of the femoral neck component. The resection guide surfaces of the surgical device indicate a Standard Offset 135° resection plane and a High Offset 135° resection plane.

This is discussed in further detail below, with respect to FIGS. 1 to 4.

Second Exemplary Hip System

Within this system, the neck length of the femoral stem component is constant for all sizes of stem having the same neck offset. Four neck variants are provided: a Standard Offset 135° variant, a High Offset 135° variant, a Short Neck Standard Offset 135° variant, and a Standard Offset 125° variant.

Two constructions of the surgical device according to the invention may be provided for use with this second exemplary hip system.

A first construction of the surgical device is configured for use with the Standard Offset 135° variant and High Offset 135° variants of the neck.

A second construction of the surgical device is configured for use with the Short Neck Standard Offset 135° variant, and a Standard Offset 125° variant.

This is discussed in further detail below with respect to FIG. 5.

Referring back to FIG. 1, the construction of the surgical device is configured for use with the first exemplary hip system. The frame is dissected by an imaginary line (dashed line) through the centrepoint into a medial portion 21 and a lateral portion 22. The frame also includes markings to indicate to the surgeon which femoral head (right or left) that the device should be mounted to when using the different surgical approaches (e.g., anterior or posterior) during hip arthroplasty. The frame also includes a marking (size 1-4) which indicates to the surgeon that this device is for use with the four sizes of femoral stem components within Group 1 of the first exemplary hip system.

The arm 30 has a medial edge 31 and a lateral edge 32.

The resection guide 40 has a first superiorly located resection guide surface 41 that corresponds to a resection plane for a standard neck offset (STD). The resection guide also has a second inferiorly located resection guide surface 42 that corresponds to a resection plane for a high offset neck (HI).

In this first construction of the surgical device 10 a section of the medial edge 31 of the arm is flat and defines the linear alignment surface 50.

Figure 2:
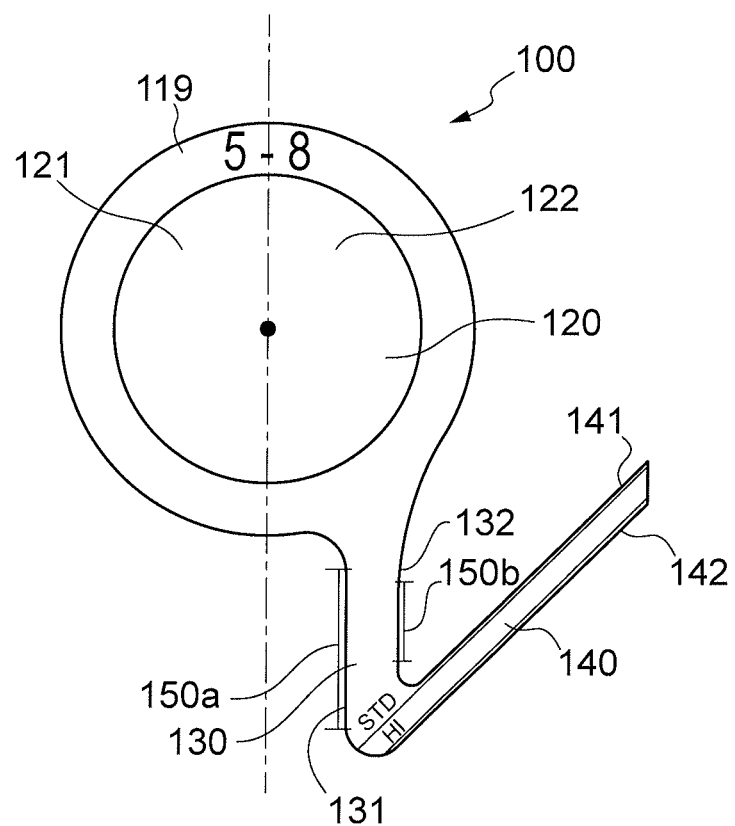
FIG. 2: Illustrates a schematic of a second exemplary construction of the surgical device according to the invention.

FIG. 2 illustrates a second construction of the surgical device 100 also configured for use with the first exemplary hip system. The device includes a frame 119 having a substantially circular aperture 120 for mounting the frame on a femoral head. The device also includes an arm 130 and a resection guide 140. The arm extends from an inferior edge of the frame to the resection guide.

The frame is dissected by an imaginary line (dashed line) through the centrepoint into a medial portion 121 and a lateral portion 122. The frame includes a marking (size 5-8) which indicates to the surgeon that this device is for use with femoral stem components within Group 2 of the first exemplary hip system.

The arm 130 has a medial edge 131 and a lateral edge 132. The length of the arm 130 in this second construction of the surgical is longer than the length of the arm 30 in the first construction of the surgical device. This ensures that correct neck length is achieved when the larger stem sizes (sizes 5, 6, 7 or 8) are used.

The resection guide 140 has a first superiorly located resection guide surface 141 that corresponds to a resection plane for a standard neck offset (STD). The resection guide also has a second inferiorly located resection guide surface 142 that corresponds to a resection plane for a high offset neck (HI). The resection guide surfaces 141, 142 are substantially parallel.

In this second construction of the surgical device 110 a section of the medial edge 131 of the arm is flat and defines a first linear alignment surface 150a. A section of the lateral edge 132 of the arm is also flat and defines a second linear alignment surface 150b. The surgeon can align either linear alignment surface 150a, 150b with the femoral shaft axis.

Figure 3:
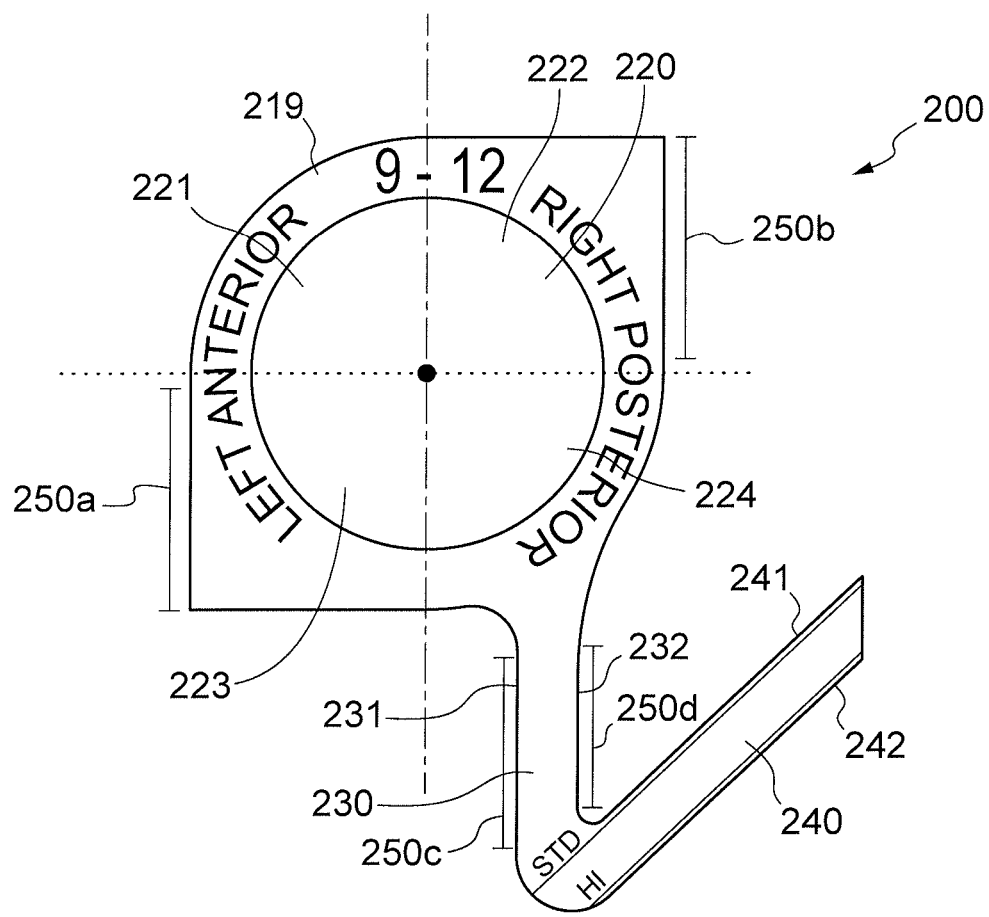
FIG. 3: Illustrates a schematic of a third exemplary construction of the surgical device according to the invention.

A third construction of the surgical device 200 is illustrated in FIG. 3. This device is also configured for use with the first exemplary hip system. The device includes a frame 219 having a substantially circular aperture 220 for mounting the frame on a femoral head. The device also includes an arm 230 and a resection guide 240. The arm extends from an inferior edge of the frame to the resection guide.

The frame 219 is dissected by a first imaginary line (dashed line) into a medial half and a lateral half. The frame is further dissected by a second imaginary line (dotted line) into a superior half and an inferior half. This forms four quadrants: a superior medial quadrant 221, a superior lateral quadrant 222, an inferior medial quadrant 223 and an inferior lateral quadrant 224.

The frame includes a marking (size 9-12), which indicates to the surgeon that this device is for use with femoral stem components within Group 3 of the first exemplary hip system.

The arm 230 has a medial edge 231 and a lateral edge 232. The length of the arm 230 in this third construction of the surgical is longer than the length of the arm 30, 130 in the first and second construction of the surgical device. This ensures that a conservative resection is achieved when the larger stem sizes of 9, 10, 11 or 12 are used.

The resection guide 240 has a first superiorly located resection guide surface 241 that corresponds to a resection plane for a standard neck offset (STD). The resection guide also has a second inferiorly located resection guide surface 242 that corresponds to a resection plane for a high offset neck (HI). The resection guide surfaces 241, 242 are substantially parallel.

In this third construction of the surgical device 200 a section of the medial edge of the inferior medial quadrant 223 is flat and defines a first linear alignment surface 250a. A section of the lateral edge of the superior lateral quadrant 222 is flat and defines a second linear alignment surface 250b. A section of the medial edge 232 of the arm is flat and defines a third linear alignment surface 250c. A section of the lateral edge 231 of the arm is flat and defines a fourth linear alignment surface 250d. A surgeon can align any one of the linear alignment surfaces 250a-250d with the femoral shaft axis.

As can be seen from FIG. 3, the superior lateral quadrant 222 and the inferior medial quadrant 223 are each provided with a square outer corner. In some constructions, only one quadrant includes a square outer corner. Optionally, a square outer corner may be provided in at least two of the quadrants of the frame. These two quadrants may be diametrically opposed. Optionally, a square outer corner may be provided in at least three of the quadrants of the frame. Optionally, a square outer corner may be provided in all the quadrants of the frame. The provision of a corner improves the stability of the device and also provides a greater surface area for the surgeon to hold the device.

Figure 4:
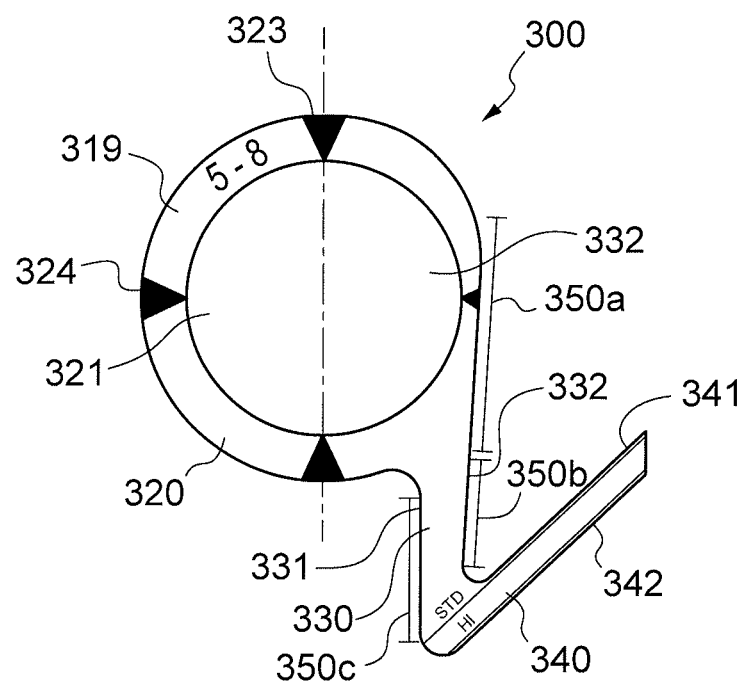
FIG. 4: Illustrates a schematic of a fourth exemplary construction of the surgical device according to the invention.

FIG. 4 shows a fourth construction of the surgical device 300. This device is also configured for use with the first exemplary hip system. The device includes a frame 319 having a substantially circular aperture 320 for mounting the frame on a femoral head, an arm 330 and a resection guide 340. The arm extends from an inferior edge of the frame to the resection guide.

The frame 319 is dissected by an imaginary line (dashed line) through the centrepoint into a medial portion 321 and a lateral portion 322. The frame includes a pair of opposed vertical arrows (323), and a pair of opposed horizontal arrows (324). These arrows help the surgeon to identify the femoral head centre.

The arm 330 has a medial edge 331 and a lateral edge 332.

The resection guide 340 has a first superiorly located resection guide surface 341 that corresponds to a resection plane for a standard neck offset (STD). The resection guide also has a second inferiorly located resection guide surface 342 that corresponds to a resection plane for a high offset neck (HI). The resection guide surfaces 341 and 342 are substantially parallel.

The fourth construction of the surgical device 300 includes three linear alignment surfaces for alignment with the femoral shaft axis. A section of the lateral edge of the lateral portion 322 of the frame is flat and defines a first linear alignment surface 350a. A section of the lateral edge 332 of the arm 330 is flat and defines a second linear alignment surface 350b. A section of the medial edge 331 of the arm 330 is flat and defines a third linear alignment surface 350c. A surgeon can align any one of the linear alignment surfaces 350a-350c with the femoral shaft axis.

Figure 5:
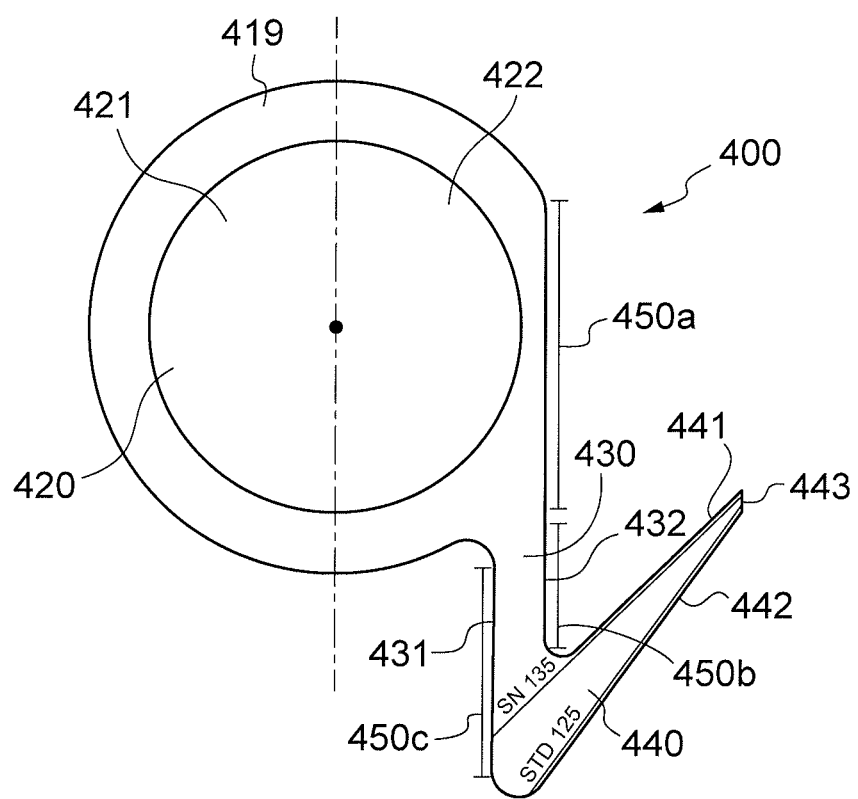
FIG. 5: Illustrates a schematic of a fifth exemplary constructions of the surgical device according to the invention.

A fifth construction of the surgical device 400 is shown in FIG. 5. This device is configured for use with the second exemplary hip system. The device includes a frame 419 having a substantially circular aperture 420 for mounting the frame on a femoral head. The device also includes an arm 430 and a resection guide 440. The arm extends from an inferior edge of the frame to the resection guide.

The frame 419 is dissected by an imaginary line (dashed line) through the centrepoint into a medial portion 421 and a lateral portion 422.

The arm 430 has a medial edge 431 and a lateral edge 432.

The resection guide 440 has a first superiorly located resection guide surface 441 that corresponds to a resection plane for a standard neck offset (STD). The resection guide also has a second inferiorly located resection guide surface 442 that corresponds to a resection plane for a high offset neck (HI). The resection guide surfaces 441 and 442 taper towards an end point 443.

The fifth construction of the surgical device 300 includes three linear alignment surfaces for alignment with the femoral shaft axis. A section of the lateral edge of the lateral portion 422 of the frame is flat and defines a first linear alignment surface 350a. A section of the lateral edge 432 of the arm 430 is flat and defines a second linear alignment surface 450b. A section of the medial edge 431 of the arm 430 is flat and defines a third linear alignment surface 450c. A surgeon can align any one of the linear alignment surfaces 450a-450c with the femoral shaft axis.

Figure 6:
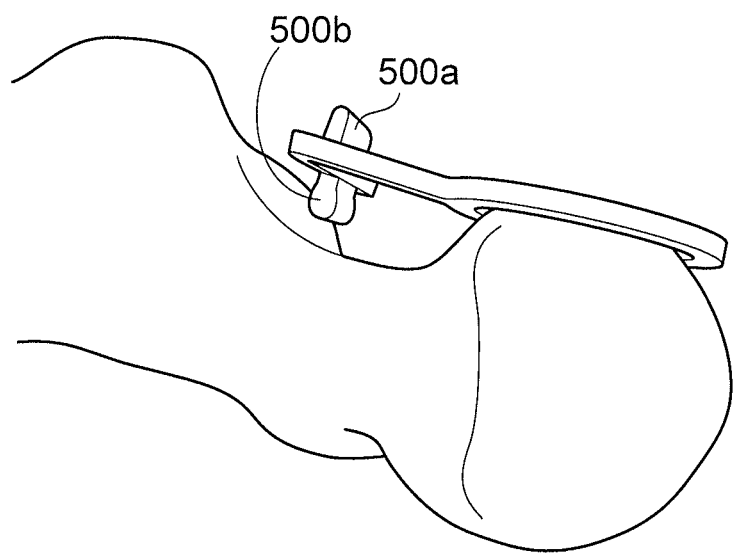
FIG. 6: Illustrates an exemplary construction of the device mounted on the femur, the surgical device including a spacer.

FIG. 6 shows the use of the surgical device according to the first, second, third and fourth constructions of the invention, in combination with a spacer. Spacer 500a is attached to the anterior surface of the frame. Spacer 500b is attached to the posterior surface of the frame. When attached to both surfaces, the surgical device can be inverted and used on the contralateral femoral head. However, the spacer can be attached to only one surface. Each block shown in FIG. 6 has a length of 10 mm and a depth of 6 mm, but this should not be taken as limiting. The spacer is used to space the resection guide away from the femoral neck and therefore minimize the error in the positioning of the resection plane, which is caused by any malorientation of the device. Accordingly, this minimizes the risk of a surgeon making a femoral neck resection this is too proximal or distal.

Figures 7A, 7B:
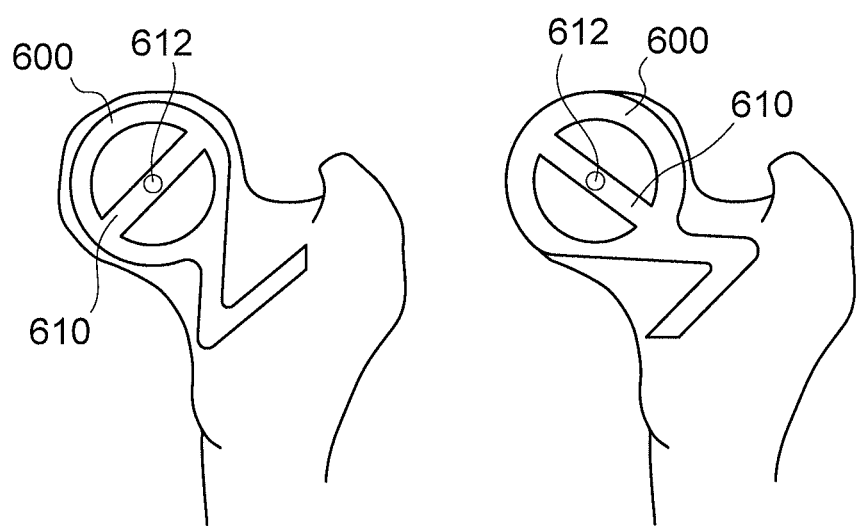
FIG. 7: Illustrates a schematic of a sixth exemplary construction of the surgical device according to the invention.

FIG. 7 illustrates a sixth construction of the surgical device 600. A bridge 610 extends between opposing sides of the frame. The bridge includes a hole 612 configured for receipt of a securing means (e.g., a bone pin or bone screw) to secure the frame to the femoral head centre. The bridge in the construction shown has a generally concave inner surface for contacting the femoral head and a generally convex outer surface. Accordingly, the orientation of the sixth construction of the neck resection guide is shown, mounted on the posterior face of the right hip (FIG. 7a), and alternatively when mounted on the anterior face of the left hip (FIG. 7b). Due to the design of the bridge, this construction of the device cannot simply be flipped over so that it can be used on the anterior aspect of the right hip and the left hip; or on the posterior aspect of both the right hip and the left hip.

Figure 8:
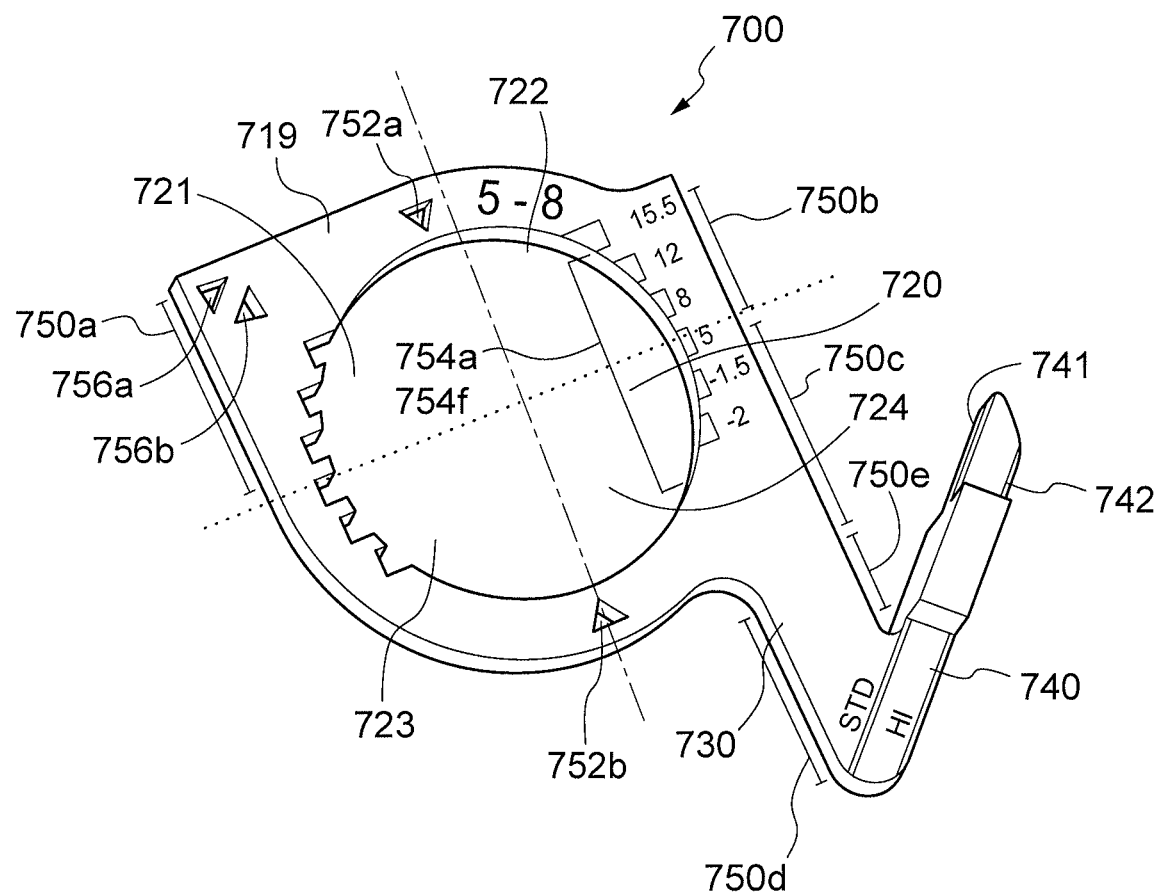
FIG. 8: Illustrates a schematic of a seventh exemplary construction of the surgical device according to the invention.

A seventh construction of the surgical device 700 is illustrated in FIG. 8. This device is also configured for use with the first exemplary hip system. The device includes a frame 719 having a substantially circular aperture 720 for mounting the frame on a femoral head. The device also includes an arm 730 and a resection guide 740. The arm extends from an inferior edge of the frame to the resection guide.

The frame includes a marking (size 5-8), which indicates to the surgeon that this device is for use with femoral stem components within Group 2 of the first exemplary hip system.

The frame is dissected by a first imaginary line (dashed line) into a medial half and a lateral half. The frame is further dissected by a second imaginary line (dotted line) into a superior half and an inferior half. This forms four quadrants: a superior medial quadrant 721, a superior lateral quadrant 722, an inferior medial quadrant 723 and an inferior lateral quadrant 724.

The frame 719 includes a pair of opposed vertical arrows 752a; 752b. These arrows visually aid the surgeon in identifying the femoral head centre.

The frame includes indicia representative of femoral offset. The indicia are provided on both the medial portion and the lateral portion of the frame.

In this construction the indicia is provided in the form of a graduated scale defined by a plurality of slots 754a-f arranged along the inner perimeter of the lateral half of frame. Each slot of the plurality of slots represents a different femoral head offset.

Each slot (primary indicia) has a numerical value (secondary indicia) associated with it. The numerical value is indicative of the femoral head offset as measured in millimetres.

The most superiorly located slot 754a represents a +15.5 mm femoral head offset. The neighbouring slot 754b, positioned inferior of slot 754a represents a +12 mm femoral head offset. The next inferiorly placed slot 754c, represents a +8 mm femoral head offset. The next inferiorly placed slot 754d, represents a +5 mm femoral head offset. The next inferiorly placed slot 754e, represents a +1.5 mm femoral head offset. Finally, the next inferiorly placed slot 754f, represents a −2 mm femoral head offset.

Identical indicia may be provided on both faces of the frame. This allows the device to simply be flipped over so that it can be used to determine the femoral head offset when mounted on the anterior aspect of the right hip and the left hip; or on the posterior aspect of the right hip and the left hip.

As can be seen from FIG. 8, the superior medial quadrant 721 is provided with a square outer corner. This is an optional feature. The provision of a square outer corner improves the stability of the device, and also provides a greater surface area for the surgeon to hold the device. In addition, this corner includes a pair of arrows 756a; 756b, with the first arrow 756a pointing in the superior-medial direction, and the second arrow 756b pointing in the inferior-lateral direction. The arrows 756a, 756b indicate to the surgeon the direction that the guide should be moved relative to the femoral head centre when aligning one of the plurality of slots 754a-f with the femoral head centre.

The resection guide 740 has a first superiorly located resection guide surface 741 that corresponds to a resection plane for a standard neck offset (STD). The resection guide also has a second inferiorly located resection guide surface 742 that corresponds to a resection plane for a high offset neck (HI). The resection guide surfaces 741, 742 are substantially parallel.

This seventh construction of the surgical device 700 includes five linear alignment surfaces for alignment with the femoral shaft axis. A section of the medial edge of the superior medial quadrant 721 is flat and defines a first linear alignment surface 750a. A section of the lateral edge of the superior lateral quadrant 722 is flat and defines a second linear alignment surface 750b. A section of the lateral edge of the inferior lateral quadrant 724 is flat and defines a third linear alignment surface 750c. A section of the medial edge 731 of the arm 730 is flat and defines a fourth linear alignment surface 750d. A section of the lateral edge 732 of the arm 730 is flat and defines a fifth linear alignment surface 750e. A surgeon can align any one of the linear alignment surfaces 750a-750e with the femoral shaft axis.

Figure 9A:
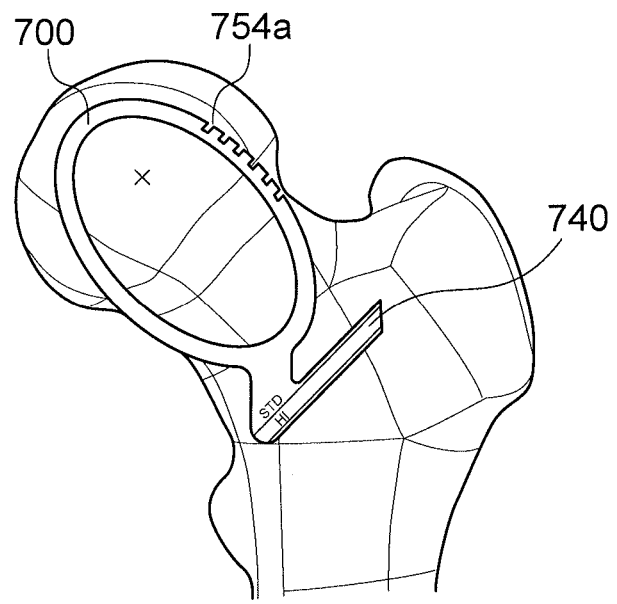
FIG. 9: Illustrates a schematic of an eighth exemplary construction of the surgical device mounted on a femoral head in a first femoral offset position (FIG. 9a), and mounted on the femoral head in a second femoral offset position (FIG. 9b)
Figure 9B:
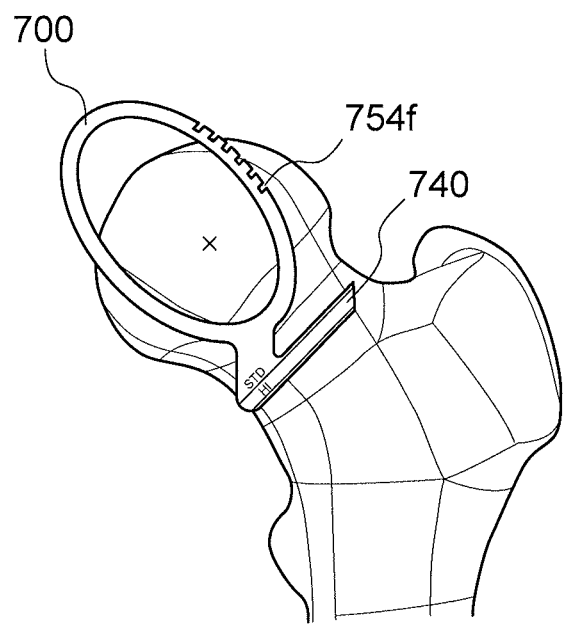

FIG. 9 shows an eighth construction of the device being used to indicate the resection plane relative to different femoral head offsets. The aperture is generally oval in shape. In FIG. 9A the guide is positioned on the femoral head so that slot 754 (i.e., representing a +15.5 mm femoral offset) is aligned with the centre of the femoral head (shown as a cross-hair). In FIG. 9B the same guide has been repositioned on the femoral head so that slot 754f (i.e., representing a −2 mm femoral offset) is aligned with the centre of the femoral head (shown as a cross-hair). It is readily apparent that in FIG. 9B the resection guide 740 is positioned superior of the resection guide in FIG. 9A.

Figure 10:
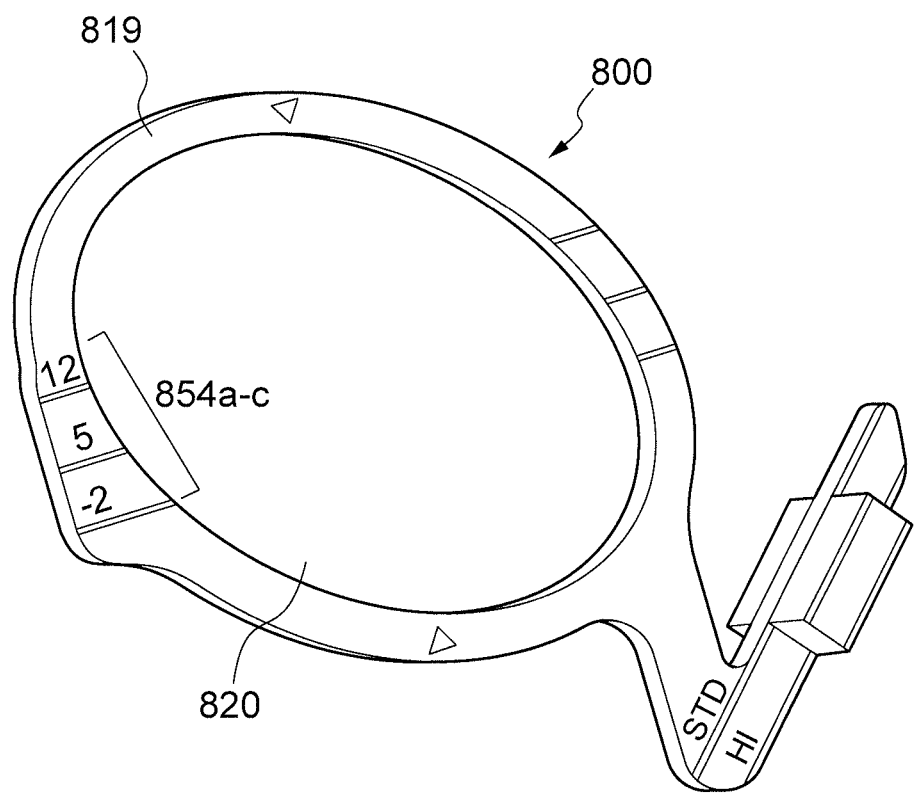
FIG. 10: Illustrates a schematic of a ninth exemplary construction of the surgical device according to the invention.

The ninth construction of the surgical device 800 as shown in FIG. 10 is similar in design to the first and second constructions shown in FIGS. 1 and 2. The device differs in that the frame 819 has a substantially oval aperture 820. This provides the device with an improved ability for movement on the femoral head.

In addition, the device includes indicia representative of femoral offset. In this construction the indicia is provided in the form of a graduated scale defined by a plurality of lines 854a-c extending between the inner perimeter and outer perimeter of the frame. Each line of the plurality of lines represents a different femoral head offset.

Each line (primary indicia) has a numerical value (secondary indicia) associated with it. The numerical value is indicative of the femoral head offset as measured in millimetres.

The guide may be used to resect conservatively at the calcar face. Accordingly, for an exemplary implant system, the femoral head offsets may be grouped such that the first femoral offset indicated by "−2 mm" on the device represents both a −2 mm and +1.5 mm femoral head offset; the second femoral offset indicated by "+5 mm" on the device represents both a +5 mm and +8 mm femoral head offset, and the third femoral offset indicated by "+12 mm" represents both a +12 mm and +17.5 mm femoral head offset.

As illustrated, the most superiorly located line 854a represents the "12 mm" femoral head offset. The neighbouring slot 854b, positioned inferior of slot 854a represents the "+5 mm" femoral head offset. The next inferiorly placed slot 854c, represents the "−2 mm" femoral head offset.

Figure 11:
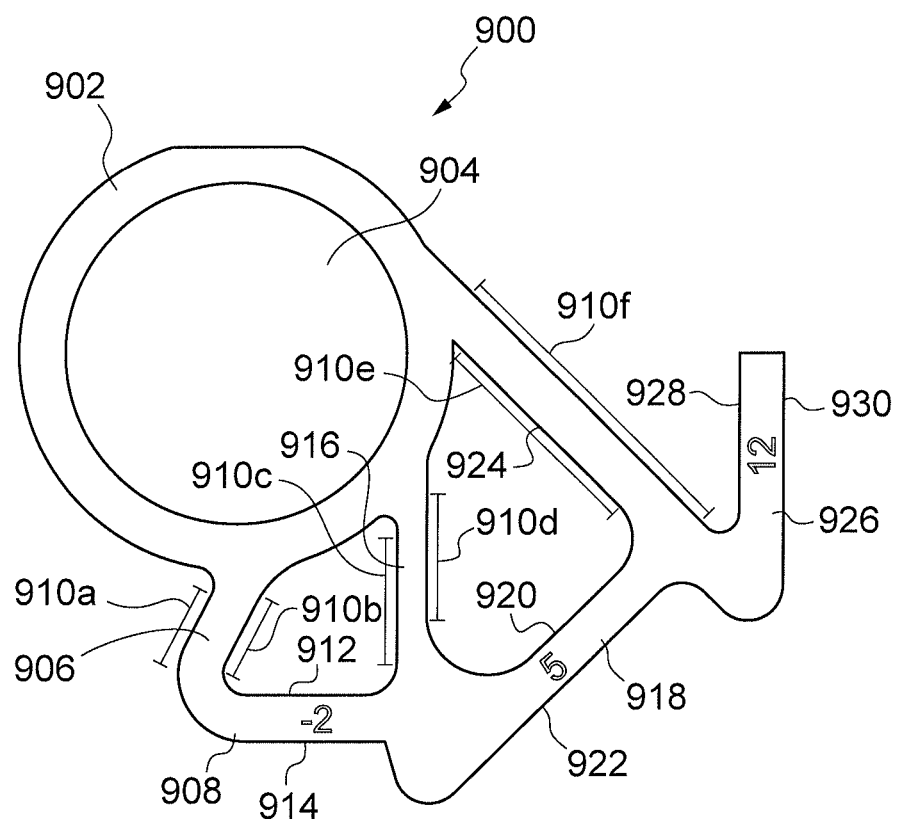
FIG. 11: Illustrates a schematic of a tenth exemplary construction of the surgical device according to the invention.

FIG. 11 shows a tenth construction of the surgical device. The device 900 includes a frame 902 having a substantially circular aperture 904 for receiving the femoral head.

A first arm 906 extends from an inferior edge of the frame 902 to a first resection guide 908 labeled "−2".

A section of the medial edge of the first arm 906 is flat and defines a first linear alignment surface 910a. A section of the lateral edge of the first arm is flat and defines a second linear alignment surface 910b.

The resection guide 908 has a first resection guide surface 912 that corresponds to a resection plane for a standard neck offset. The resection guide also has a second resection guide surface 914 that corresponds to a resection plane for a high neck offset. The resection guide surfaces 912, 914 are substantially parallel.

When the first and second linear alignment surfaces 910a, 910b are aligned with the femoral shaft axis, the first resection guide 908 can be used to indicate the position of a conservative standard (along the resection guide surface 912) or high neck offset resection plane (along the resection guide surface 914) for achieving a −2 mm or a +1.5 mm femoral head offset.

The device also includes a second arm 916 laterally placed relative to the first arm about the frame 902, and extending from an inferior edge of the frame. The second arm forms a bridge between the frame 902 and a second resection guide 918. The second resection guide is labeled "5". A section of the medial edge of the second arm is flat and defines a third linear alignment surface 910c. A section of the lateral edge of the second arm is flat and defines a fourth linear alignment surface 910d.

The second resection guide 918 has a third resection guide surface 920 that corresponds to a resection plane for a standard neck offset. The resection guide also has a fourth resection guide surface 922 that corresponds to a resection plane for a high neck offset. The resection guide surfaces 920, 922 are substantially parallel.

When the third and fourth linear alignment surfaces 910c, 910d are aligned with the femoral shaft axis, the second resection guide 918 indicates a conservative standard or high offset neck resection plane for achieving a +5 mm or a +8 mm femoral head offset.

The device also includes a third arm 924 that is laterally placed relative to the second arm about the frame 902, and extending from an inferior edge of the frame. The third arm 924 forms a bridge between the frame 902 and a third resection guide 926. The third resection guide is labeled "12". A section of the medial edge of the third arm is flat and defines a fifth linear alignment surface 910e. A section of the lateral edge of the third arm is flat and defines a sixth linear alignment surface 910f.

The resection guide 926 has a fifth resection guide surface 928 that corresponds to a resection plane for a standard neck offset. The resection guide also has a sixth resection guide surface 930 that corresponds to a resection plane for a high neck offset. The resection guide surfaces 928, 930 are substantially parallel.

When the fifth and sixth linear alignment surfaces are aligned with the femoral shaft axis, the third resection guide 926 indicates the position of a conservative standard or high offset neck resection plane for achieving a +12 mm and +17.5 mm femoral head offset.

Figure 12:
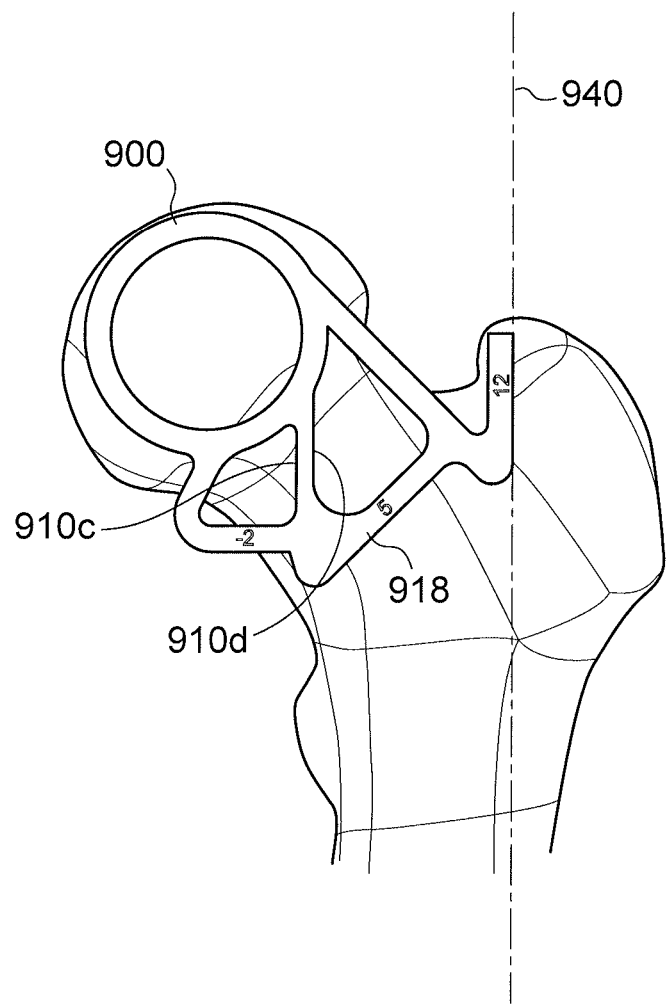
FIG. 12: Illustrates the device of FIG. 11 mounted on a femoral head.

FIG. 12 shows the device 900 of FIG. 11 mounted on a femoral head. In order to identify the resection plane necessary to achieve a "+5 mm" femoral head offset the surgeon may be rotate the device whilst it is mounted on the femoral head until the third and fourth linear alignment surfaces 910c 910d on the second arm 912 are aligned with the femoral shaft axis. The surgeon can then use the resection guide 918 to mark either a high or standard offset resection plane on the femoral neck.

Figure 13A:
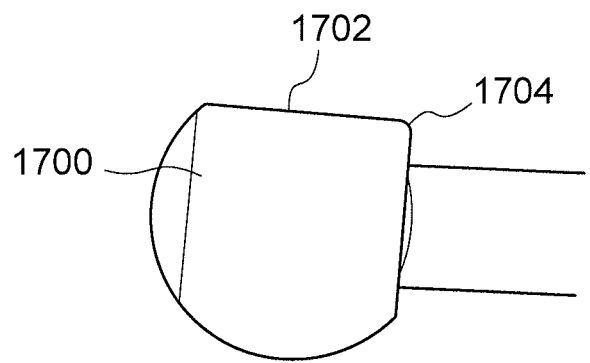
FIG. 13: Illustrates an exemplary trial femoral head for use during a controlled resection of the neck of a femur during a hip replacement procedure.
Figure 13B:
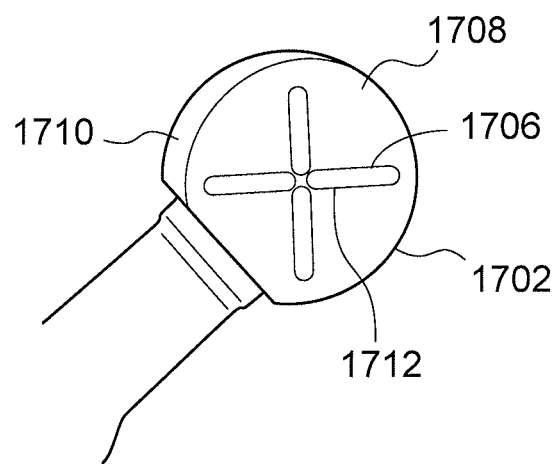

FIG. 13 shows an exemplary trial femoral head 1700 for use in hip arthroplasty. The trial femoral head includes a planar portion 1702 provided on its posterior aspect 1704. A cross 1706 that is defined by a vertical line 1708 and a horizontal line 1710 is provided on the planar portion 1702. The intersection of the vertical line 1708 and the horizontal line 1710 indicates the femoral head centre 1712 of the trial femoral head.

Figure 14:
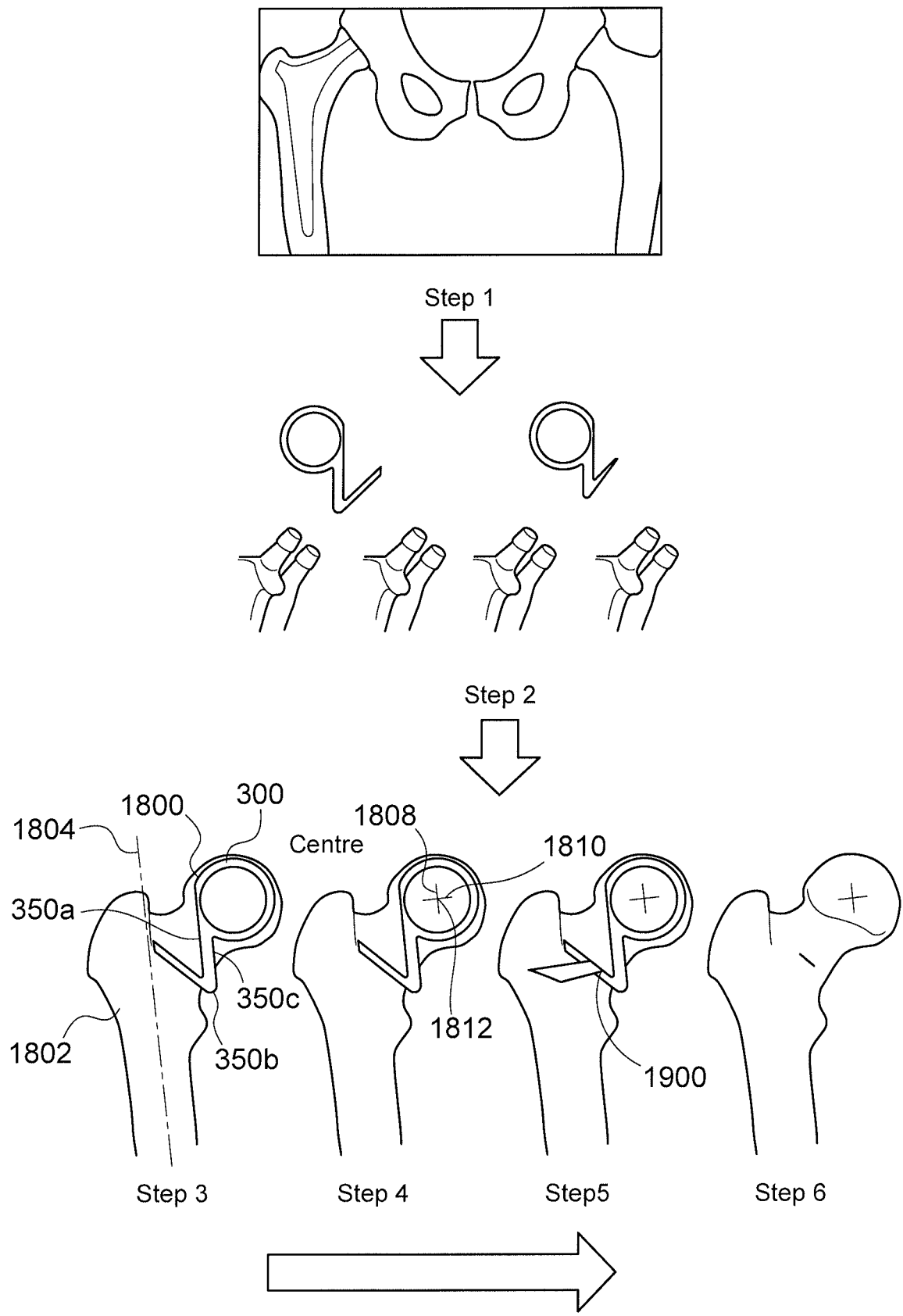
FIG. 14: Illustrates an exemplary surgical method for performing a controlled resection of the neck of a femur during a hip replacement procedure.
Figure 14:
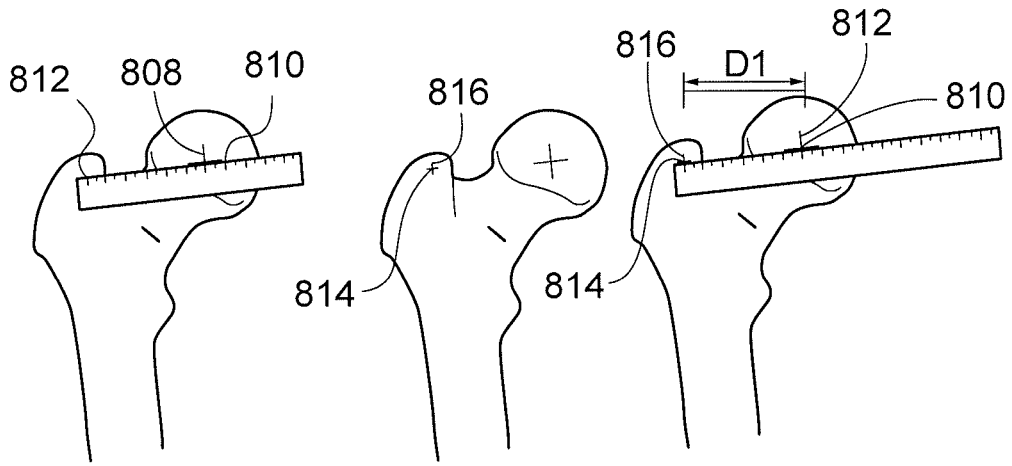
Figure 14:
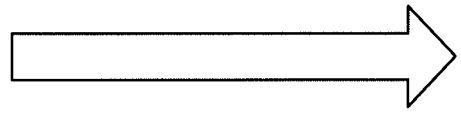
Figure 14:
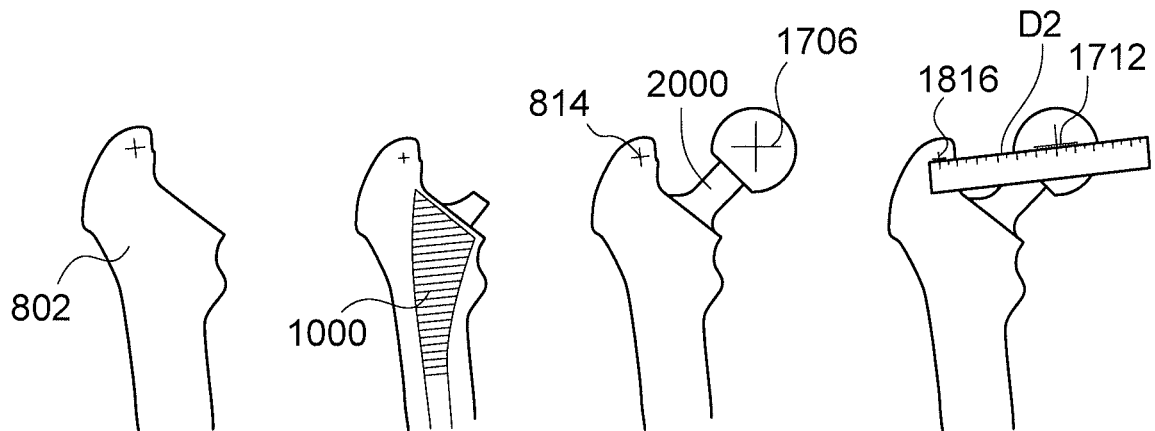
Figure 14:
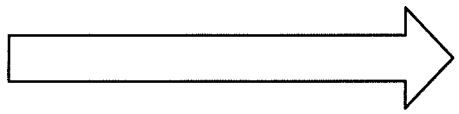

A surgical technique is provided in FIG. 14, which comprises the following steps:
  Step 1: Provide an image of the hip;
  Step 2: Chose an appropriate neck resection guide. The guide 300 shown here is the fourth exemplary construction of the surgical device according to the invention;
  Step 3: Place the neck resection guide 300 on the posterior aspect of the left native femoral head 1800 and neck 1802—emphasizing that the linear alignment surfaces 350a, 350b, 350c are parallel with the femoral axis 1804;

Step 4: When the frame is centred on the native femoral head 1800, use a marker pen to place a vertical line 1808 and a horizontal line 1810 on the native femoral head that will intersect at the femoral head centre 1812;

Step 5: Use an osteotome 1900 to mark the level of neck resection, either standard or high offset;

Step 6: Remove the neck resection guide;

Step 7: Use a rule placed parallel to the horizontal line 1810 on the native femoral head and make a further horizontal line 1814 on the adjacent greater trochanter;

Step 8: At a chosen point on the horizontal line 1814 on the greater trochanter make a vertical mark 1816. Record the dimension $D_1$ from the femoral head centre 1812 to the vertical mark 1816 on the greater trochanter;

Step 9: Resect the native femoral head;

Step 10: Prepare the femur with broaches 1000 to chosen size and depth;

Step 11: Place a trial neck and head 2000 onto the broach; advantageously the trial femoral head of FIG. 8 is used;

Step 12: Ensure that the horizontal line 1706 of the trial femoral head is aligned with the horizontal line 1814 on the greater trochanter. The alignment of the two horizontal lines 1706, 1814 ensures that the vertical height of the trial femoral head is consistent with the vertical height of the native femoral head. Then, measure the distance $D_2$ from the femoral head centre 1712 of the trial femoral head to the vertical line 1816 on the greater trochanter. If/when $D_1$ is substantially the same as $D_2$, the surgeon knows that the anatomic femoral head offset is effectively restored by the chosen trial prosthetic head.

The performance of the surgical procedure is not limited to the surgical steps as listed above, or to any specific order of performance of the steps. The steps may be performed in an order according to surgeon preference.

Figure 15:
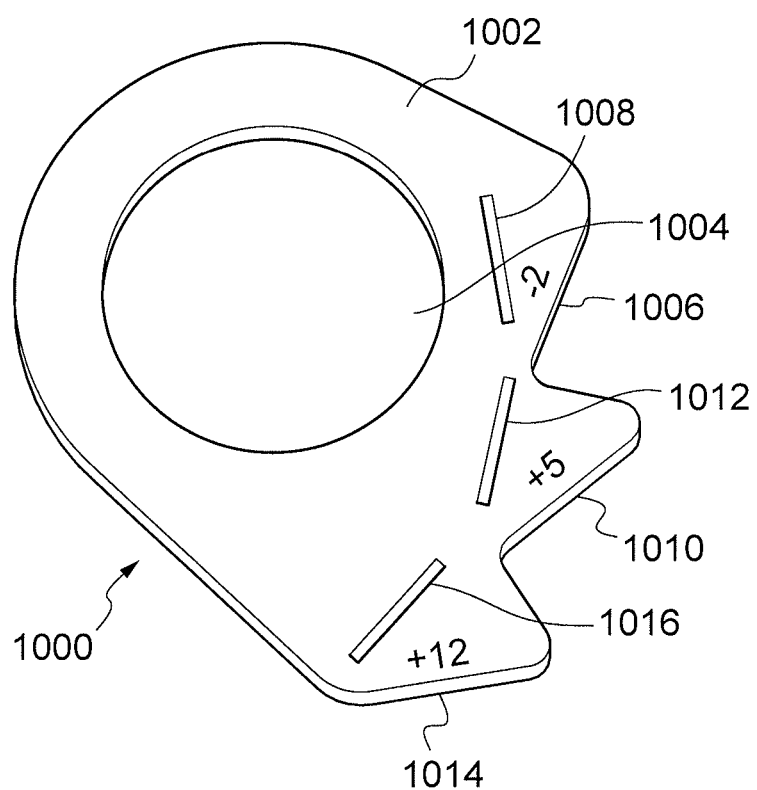
FIG. 15: Illustrates another construction of a surgical device for use in indicating the resection plane relative to different femoral head offsets.

FIG. 15 another construction of a surgical device 1000 for use in indicating the resection plane relative to different femoral head offsets. The device includes a frame 1002 having a substantially circular aperture 1004 for receiving the femoral head.

The device 1000 includes a first resection guide surface 1006 labeled "−2 mm". Associated with this surface is an alignment reference marker 1008 for alignment with the femoral shaft axis. In the construction shown, the alignment reference marker is in the form of a black line, that may be printed onto the surface of the device.

In order to identify the resection plane necessary to achieve a "−2 mm" femoral head offset the surgeon may be rotate the device whilst it is mounted on the femoral head until the alignment reference marker 1008 is aligned with the femoral shaft axis. The surgeon can then use the resection guide surface 1006 to mark the standard offset resection plane on the femoral neck.

The device also includes a second resection guide surface 1010 labeled "+5 mm". Associated with this surface is an alignment reference marker 1012 for alignment with the femoral shaft axis. In the construction shown, the alignment reference marker is in the form of a black line, that may be printed onto the surface of the device.

In order to identify the resection plane necessary to achieve a "+5 mm" femoral head offset the surgeon may be rotate the device whilst it is mounted on the femoral head until the alignment reference marker 1012 is aligned with the femoral shaft axis. The surgeon can then use the resection guide surface 1010 to mark the standard offset resection plane on the femoral neck.

The device also includes a third resection guide surface 1014 labeled "+12 mm". Associated with this surface is an alignment reference marker 1016 for alignment with the femoral shaft axis. In the construction shown, the alignment reference marker is in the form of a black line, that may be printed onto the surface of the device.

In order to identify the resection plane necessary to achieve a "+12 mm" femoral head offset the surgeon may be rotate the device whilst it is mounted on the femoral head until the alignment reference marker 1016 is aligned with the femoral shaft axis. The surgeon can then use the resection guide surface 1014 to mark the standard offset resection plane on the femoral neck.

The construction can be similarly marked on both the upper and lower surfaces. As such, the device can simply be flipped over and used on the other hip. Although particular constructions of the invention have been described, it will be appreciated that many modifications/additions and/or substitutions may be made within the scope of the claimed invention.

The invention claimed is:

1. A surgical device for performing a controlled resection of a neck of a femur during a hip replacement procedure, the surgical device comprising:
a body portion having:
a frame comprising an aperture, wherein the aperture is dimensioned for receiving a femoral head of the femur to position the body portion with respect to a centre of the femoral head;
a resection guide for indicating a position of a resection plane on the femoral neck, and
an arm extending between the frame and the resection guide,
wherein the body portion includes a linear alignment surface for alignment with a femoral shaft axis of the femur while the frame is mounted on the femoral head; and
wherein the frame has a medial portion and a lateral portion and wherein the linear alignment surface is provided on either the medial portion or the lateral portion.

2. The surgical device of claim 1, wherein the frame has more than one linear alignment surface and wherein a linear alignment surface is provided on the medial portion and a linear alignment surface is provided on the lateral portion.

3. The surgical device of claim 1, wherein the resection guide includes a guide slot for indicating a position of a resection plane on the femoral neck.

4. The surgical device of claim 3, wherein the guide slot is a cutting slot for receiving a blade of a cutting device during said resection of the neck.

5. The surgical device of claim 1, wherein the resection guide tapers.

6. The surgical device of claim 1, wherein the resection guide has a first surface and a second opposing surface, and wherein a spacer is provided on at least one of the first surface and the second opposing surface for spacing the resection guide apart from the femoral neck.

7. The surgical device of claim 6, wherein the spacer is removably mountable on the resection guide.

8. The surgical device of claim 1, wherein the aperture is substantially oval.

9. The surgical device of claim 1, wherein the frame includes a pin hole configured for removable receipt of a bone pin for removably mounting the frame on the femoral head.

10. The surgical device of claim 1, wherein the body portion has one or more additional linear alignment surface; wherein the arm has a medial edge and a lateral edge; and wherein the additional linear alignment surface is provided one or both of the medial edge or the lateral edge.

11. A surgical device for performing a controlled resection of a neck of a femur during a hip replacement procedure, the surgical device comprising:
a body portion having:
a frame comprising an aperture, wherein the aperture is dimensioned for receiving a femoral head of the femur to position the body portion with respect to a centre of the femoral head;
a resection guide for indicating a position of a resection plane on the femoral neck, and
an arm extending between the frame and the resection guide,
wherein the body portion includes a linear alignment surface for alignment with a femoral shaft axis of the femur while the frame is mounted on the femoral head; and
wherein the arm has a medial edge and a lateral edge and wherein the linear alignment surface is provided on either the medial edge or the lateral edge.

12. The surgical device of claim 11, wherein the arm has more than one linear alignment surface, and wherein a linear alignment surface is provided on the medial edge of the arm and a linear alignment surface is provided on the lateral edge of the arm.

13. The surgical device of claim 11, wherein the frame has a medial portion and wherein a linear alignment surface is provided on the medial portion of the frame and a linear alignment surface is provided on the medial edge of the arm.

14. The surgical device of claim 13, wherein the linear alignment surface on the frame and the linear alignment surface on the arm are collinear.

15. The surgical device of claim 11, wherein the frame has a lateral portion and wherein a linear alignment surface is provided on the lateral portion of the frame and a linear alignment surface is provided on the lateral edge of the arm.

16. The surgical device of claim 15, wherein the linear alignment surface on the frame and the linear alignment surface on the arm are collinear.

17. The surgical device of claim 11, wherein the resection guide includes a guide slot for indicating a position of a resection plane on the femoral neck.

18. The surgical device of claim 17, wherein the guide slot is a cutting slot for receiving a blade of a cutting device during said resection of the neck.

19. The surgical device of claim 11, wherein the resection guide tapers.

20. The surgical device of claim 11, wherein the resection guide has a first surface and a second opposing surface, and wherein a spacer is provided on at least one of the first surface and the second opposing surface for spacing the resection guide apart from the femoral neck.

21. The surgical device of claim 20, wherein the spacer is removably mountable on the resection guide.

22. The surgical device of claim 11, wherein the aperture is substantially oval.

23. The surgical device of claim 11, wherein the frame includes a pin hole configured for removable receipt of a bone pin for removably mounting the frame on the femoral head.

24. A surgical kit for use in performing a controlled resection of a neck of a femur during a hip replacement procedure, the surgical kit comprising a first surgical device comprising:
a body portion having:
a frame comprising a medial portion, a lateral portion and an aperture, wherein the aperture is dimensioned for receiving a femoral head of the femur to position the body portion with respect to a centre of the femoral head;
a resection guide for indicating a position of a resection plane on the femoral neck, and
an arm extending between the frame and the resection guide, the arm comprising a medial edge and a lateral edge;
wherein the body portion includes a linear alignment surface for alignment with a femoral shaft axis of the femur whilst the frame is mounted on the femoral head, and
a second surgical device comprising:
a body portion having:
a frame comprising a medial portion, a lateral portion and an aperture, wherein the aperture is dimensioned for receiving a femoral head of the femur to position the body portion with respect to a centre of the femoral head;
a resection guide for indicating a position of a resection plane on the femoral neck, and
an arm extending between the frame and the resection guide, the arm comprising a medial edge and a lateral edge;
wherein the body portion of each of the first surgical device and the second surgical device includes one or more linear alignment surfaces for alignment with a femoral shaft axis of the femur whilst the frame of the first surgical device or the second surgical device is mounted on the femoral head, and wherein the arm of the first device has a first length as measured between the frame and resection guide, and the arm of the second device has a second length as measured between the frame and resection guide, and wherein the first length and the second length are different;
wherein the one or more linear alignment surfaces is provided on one or both of the frame and the arm of the first surgical device and on one or both of the frame and the arm of the second surgical device; and
wherein, when a linear alignment surface of the one or more linear alignment surfaces is provided on the frame of the first surgical device or the second surgical device, the linear alignment surface is provided on one or both of the medial portion or the lateral portion; and
wherein, when a linear alignment surface of the one or more linear alignment surfaces is provided on the arm of the first surgical device or the second surgical device, the linear alignment surface is provided on one or both of the medial edge or the lateral edge.

\* \* \* \* \*